US011612613B2

(12) United States Patent
Petcavich (10) Patent No.: US 11,612,613 B2
(45) Date of Patent: Mar. 28, 2023

(54) FORMULATIONS FOR THE DELIVERY OF AUTOPHAGY STIMULATING TREHALOSE (71) Applicant: Robert Petcavich, The Woodlands, TX (US)

(72) Inventor: Robert Petcavich, The Woodlands, TX (US)

(*) Notice: Subject to any disclaimer, the term of this patent is extended or adjusted under 35 U.S.C. 154(b) by 0 days.

(21) Appl. No.: 16/637,853

(22) PCT Filed: Aug. 8, 2018

(86) PCT No.: PCT/US2018/045784
§ 371 (c)(1),
(2) Date: Feb. 10, 2020

(87) PCT Pub. No.: WO2019/032685
PCT Pub. Date: Feb. 14, 2019

(65) Prior Publication Data
US 2020/0246363 A1    Aug. 6, 2020

Related U.S. Application Data (60) Provisional application No. 62/542,328, filed on Aug. 8, 2017.

(51) Int. Cl.
A61K 31/7016    (2006.01)
A61K 9/00       (2006.01)
A61K 31/436     (2006.01)
A61K 31/155     (2006.01)

(52) U.S. Cl.
CPC .......... *A61K 31/7016* (2013.01); *A61K 9/006* (2013.01); *A61K 9/0056* (2013.01); *A61K 9/0075* (2013.01); *A61K 31/155* (2013.01); *A61K 31/436* (2013.01)

(58) Field of Classification Search
CPC .. A61K 9/006; A61K 31/7016; A61K 31/155; A61K 9/0075; A61K 9/0056; A61K 31/436; A61K 2300/00
See application file for complete search history.

(56) References Cited

U.S. PATENT DOCUMENTS 7,022,311 B1 * 4/2006 Ohkuma .............. A61K 9/0075
                                               424/45
8,226,928 B1   7/2012 Sung et al.
2012/0015901 A1 * 1/2012 Winderickx ............ A61P 17/02
                                                514/53
2015/0265570 A1   9/2015 Tong

FOREIGN PATENT DOCUMENTS

WO    WO-2012066319 A1      5/2012
WO    WO-2017127641 A1 *    7/2017  .............. A61P 25/00

* cited by examiner

*Primary Examiner* — Jianfeng Song
(74) *Attorney, Agent, or Firm* — Feeney IP Law; Alan F. Feeney

(57) ABSTRACT

A pharmaceutically acceptable composition comprising trehalose and a pharmaceutically acceptable excipient and methods of delivering autophagy stimulating trehalose to a patient in need thereof.

8 Claims, 3 Drawing Sheets

FORMULATIONS FOR THE DELIVERY OF AUTOPHAGY STIMULATING TREHALOSE

CROSS-REFERENCE TO RELATED APPLICATIONS

This application is a continuation under 35 U.S.C. § 371 of International Application No. PCT/US2018/045784 filed on Aug. 8, 2018 which claims priority to and the benefit of U.S. Provisional Patent Application No. 62/542,328 filed Aug. 8, 2017. The entire contents of each are incorporated by reference herein.

BACKGROUND OF THE INVENTION

The macrophage is a central player in atherosclerotic progression. Insidious macrophage infiltration of the nascent plaque, phagocytosis of deposited lipid and cellular debris, foam cell formation, and progressive macrophage dysfunction and inflammatory signaling constitute some of the major events during atherogenesis. Understanding the cellular processes that underlie macrophage dysfunction remains an important area of investigation both scientifically and clinically, serving as the basis for future therapeutics. An area that has garnered substantial recent focus is autophagy, a highly evolutionarily conserved process with critical roles in the degradation and recycling of long-lived/damaged intracellular material including accumulated lipids and plaque. Recently, it has been demonstrated that macrophage mediated autophagy, or lack thereof, plays a role in degenerative diseases such as cardiovascular atherosclerosis (CA), Parkinson's (PD), Huntington's (HD), Amyotrophic lateral sclerosis (ALS), and Alzheimer's (AD).

Macrophages specialize in removing lipids and debris present in the atherosclerotic plaque. Plaque progression in CA, however, renders macrophages unable to degrade exogenous atherogenic material and endogenous cargo including dysfunctional proteins and organelles. A decline in the autophagy-lysosome system contributes to this as evidenced by a derangement in key autophagy markers in both mouse and human atherosclerotic plaques. By augmenting macrophage Transcription Factor EB (TFEB), the master transcriptional regulator of autophagy-lysosomal biogenesis, it is possible to reverse the autophagy dysfunction of plaques, enhance aggrephagy of enriched protein aggregates and blunt macrophage apoptosis and pro-inflammatory signal levels, leading to reduced atherosclerosis. To harness this degradative response therapeutically, Trehalose, a natural sugar, induces macrophage autophagy-lysosomal biogenesis and recapitulates the atheroprotective properties of macrophage TFEB overexpression.

Trehalose, a disaccharide present in many non-mammalian species, protects cells against various environmental stresses. Whereas some of the protective effects may be explained by its chemical chaperone properties, its actions are largely unknown. Trehalose functions as an mTOR-independent autophagy activator. Trehalose-induced autophagy enhances the clearance of autophagy substrates like mutant huntingtin and the A30P and A53T mutants of synuclein protein, associated with Huntington disease (HD) and Parkinson disease (PD), respectively. Furthermore, Trehalose and mTOR inhibition by rapamycin together exert an additive effect on the clearance of these aggregate-prone proteins because of increased autophagic activity. By inducing autophagy, Trehalose also protects cells against subsequent pro-apoptotic insults via the mitochondrial pathway. The dual protective properties of Trehalose (as an inducer of autophagy and chemical chaperone) and the combinatorial strategy with rapamycin are relevant to the treatment of HD and related diseases where the mutant proteins are autophagy substrates.

Amyotrophic lateral sclerosis (ALS) is a fatal motoneuron disease with no current effective treatment. Accumulation of abnormal protein inclusions containing SOD1, TARDBP, FUS, among other proteins, is a pathological hallmark of ALS. Autophagy is the major degradation pathway involved in the clearance of damaged organelles and protein aggregates. Although autophagy has been shown to efficiently degrade ALS-linked mutant protein in cell culture models, several studies suggest that autophagy impairment may also contribute to disease pathogenesis. Studies have shown the potential use of Trehalose, a disaccharide that induces mTOR-independent autophagy, in the development of experimental ALS. Administration of Trehalose to mutant SOD1 transgenic mice significantly prolonged life span and attenuated the progression of disease signs. These effects were associated with decreased accumulation of SOD1 aggregates and enhanced motoneuron survival. The protective effects of Trehalose were associated with increased autophagy levels in motoneurons. Cell culture experiments demonstrated that Trehalose led to mutant SOD1 degradation by autophagy in NSC34 motoneuron cells and protected primary motoneurons against the toxicity of conditioned media from mutant SOD1 transgenic astrocytes. At the mechanistic level, Trehalose treatment led to a significant upregulation in the expression of key autophagy-related genes at the mRNA level including Lc3, Becn1, Sqstm1 and Atg5. Consistent with these changes, Trehalose administration enhanced the nuclear translocation of FOXO1, an important transcription factor involved in the activation of autophagy in neurons, suggesting a potential use of Trehalose and enhancers of mTOR-independent autophagy for the treatment of ALS.

Trehalose is a non-reducing disaccharide found in many organisms, including bacteria, yeast, fungi, insects, invertebrates, and plants capable of crossing the blood brain barrier. Trehalose is the natural hemolymph sugar of invertebrates that functions to protect the integrity of cells against various environmental stresses like heat, cold, desiccation, dehydration, and oxidation by preventing protein denaturation. Many of the stress-protecting properties of Trehalose were discovered in yeast; however, Trehalose also has beneficial effects in mammals where it is not endogenously synthesized. For instance, Trehalose may be a valuable tool for cryopreservation of cells. It is not clear how Trehalose mediates many of its protective effects, but some may be via its ability to act as chemical chaperone and influence protein folding through direct protein-Trehalose interactions.

Trehalose inhibits amyloid formation of insulin in vitro and prevents aggregation of amyloid plaques and tau tangles associated with Alzheimer's disease.

Given all the beneficial effects of Trehalose, advancing Trehalose to a clinical setting has been challenging since most previous results were achieved by peritoneal injection not oral administration. Unfortunately, during oral ingestion of Trehalose, the gut microbiome, intestine, and liver trehalase enzymes quickly degrade Trehalose into glucose rendering its therapeutic effectiveness to nil. There is no motivation or reason that potential patients will accept needle injection or intravenous administration of a therapeutic, such as Trehalose, to mitigate cardiovascular or neurodegenerative diseases. Therefore, the problem solved by the present invention is to enable an aerosol or transmucosal delivery system for Trehalose for therapeutic administration against degenerative diseases that is low cost, fast, easy to use and effective.

BRIEF SUMMARY OF THE INVENTION

An objective of the present invention is to provide a therapeutic delivery and dose system for Trehalose via an aerosol.

Another objective of this invention is to provide therapeutically effective Trehalose dose via the lungs to mitigate chronic cardiovascular and neuro degenerative diseases.

Another objective of the present invention is to provide a therapeutically effective Trehalose dose via the lungs that bypasses the digestive system.

Yet another objective of the present invention is to package the Trehalose into a one-time metered dose capsule for administration via a dry powder inhaler.

A further objective of the present invention is to provide a therapeutic delivery and dose system for Trehalose via oral mucosa delivery.

Yet another objective of this example of the invention is to provide therapeutically effective Trehalose dose via the oral mucosa to mitigate chronic cardiovascular, liver and neuro degenerative diseases.

And yet another objective of this example of the present invention is to provide a therapeutically effective Trehalose dose via the oral mucosa that bypasses the digestive system.

Yet another objective of this example is to package the Trehalose into a metered dose formulation for oral mucosa administration.

In yet another objective of the present invention is to package and combine Trehalose with other known therapeutics to amplify autophagy systemic effects of the individual therapeutic compounds.

A further objective of the present invention is to package and combine Trehalose with other known therapeutics to amplify autophagy systemic effects of an individual by combining with an immune suppressive drug such as rapamycin and/or metformin.

In another aspect, disclosed herein are pharmaceutical compositions comprising Trehalose and a pharmaceutically acceptable excipient.

Another aspect of the disclosure relates to a kit comprising the pharmaceutical composition comprising Trehalose and instructions for use thereof.

BRIEF DESCRIPTION OF THE SEVERAL VIEWS OF THE DRAWINGS

FIG. 1 shows a diagram of a dry powder inhaler that is one example of the present invention;

FIG. 2 is a schematic diagram of the autophagy process; and

FIG. 3 is a mechanism graphic for the Trehalose autophagy process.

DETAILED DESCRIPTION OF THE INVENTION

Definitions

For convenience, certain terms employed in the specification, examples and appended claims are collected here. These definitions should be read in light of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. The term "and/or" as used herein is defined as the possibility of having one or the other or both. For example, "A and/or B" provides for the scenarios of having just A or just B or a combination of A and B. If the claim reads A and/or B and/or C, the composition may include A alone, B alone, C alone, A and B but not C, B and C but not A, A and C but not B or all three A, B and C as components.

The term "autophagy", as used herein, refers to a normal physiological process in the body that deals with the destruction of cells in the body. It maintains homeostasis or normal functioning of cells by protein degradation and turnover of the destroyed cell organelles for new cell formation as depicted in FIG. 2. During cellular stress, the process of autophagy is increased and up-regulated. Autophagy induced by Trehalose is depicted in FIG. 3.

The term "bioavailable" is art-recognized and refers to a form of the subject disclosure that allows for it, or a portion of the amount administered, to be absorbed by, incorporated to, or otherwise physiologically available to a subject or patient to whom it is administered.

The term "including", as used herein, is used to mean "including but not limited to". "Including" and "including but not limited to" are used interchangeably.

The terms "inhaled administration", "inhale", "inhaled", "inhalation" or "inhalation therapy", which may be used interchangeably and as used herein, include administration of a substantially uniform distribution of appropriately sized particles to the respiratory epithelium of the nose, central airways, the peripheral aspect of the lung and/or the alveolar region of the lung or by intratracheal instillation. Such particles may be introduced to the patient and/or produced using an appropriate device, preferably a DPI.

The term "patient," "subject" or "host" to be treated by the subject method may mean either a human or non-human animal. Non-human animals include companion animals (e.g. cats, dogs) and animals raised for consumption (i.e. food animals), such as cows, pigs, chickens)

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as dextrose, lactose, glucose and sucrose; (2) starches, such as corn starch and potato starch; (3) cellulose, and its derivatives, such as microcrystalline cellulose, sodium carboxymethyl cellulose, methyl cellulose, ethyl cellulose, hydroxypropylmethyl cellulose (HPMC), and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate, glyceryl behenate and ethyl laurate; (13) agar; (14) buffering agents, such as magnesium hydroxide and aluminum hydroxide; (15) alginic acid; (16)

pyrogen-free water; (17) isotonic saline; (18) Ringer's solution; (19) ethyl alcohol; (20) phosphate buffer solutions; and (21) other non-toxic compatible substances employed in pharmaceutical formulations. The disclosed excipients may serve more than one function. For example, fillers or binders may also be disintegrants, glidants, anti-adherents, lubricants, sweeteners and the like.

The term "pharmaceutically-acceptable salts", as used herein, is art-recognized and refers to the relatively non-toxic, inorganic and organic acid addition salts, or inorganic or organic base addition salts of compounds, including, for example, those contained in compositions of the present invention.

The term "therapeutic agent", as used herein, is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physician's Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

The term "therapeutic effect", as used herein, is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The term "treating", as used herein, includes any effect, e.g., lessening, reducing, modulating, or eliminating, that results in the improvement of the condition, disease, disorder and the like.

The term "Trehalose" (also known as mycose or tremalose), as used herein, refers to a natural α-linked disaccharide formed by an α, α-1,1-glucoside bond between two α-glucose units ($C_{12}H_{22}O_{11}$) having the following formula:

(2R,3S,4S,5R,6R)-2-(Hydroxymethyl)-6-[(2R,3R,4S,5S,6R)-3,4,5-trihydroxy-6-(hydroxymethyl)oxan-2-yl]oxyoxane-3,4,5-triol Abbreviations Abbreviations used herein are defined as follows:
AD Alzheimer's Disease
AI Active Ingredient
ALS Amyotrophic Lateral Sclerosis
CA Cardiovascular Atherosclerosis
COPD Chronic Obstructive Pulmonary Disease
DPI Dry-powder inhalation
FOXO1 Forkhead box protein O1 also known as forkhead in rhabdomyosarcoma
FUS Fused in Sarcoma
GI Gastrointestinal
GRAS Generally Recognized As Safe
HD Huntington's Disease
IV Intravenous therapy
MAO Monoamine Oxidase
MDI Metered-dose inhaler
mRNA messenger RNA
mTOR mammalian Target Of Rapamycin
PD Parkinson's Disease
SL Sublingual
SOD1 Superoxide dismutase 1
TARDBP TAR DNA-binding protein 43
TFEB Transcription factor EB The oral cavity is an attractive site for the delivery of drugs either locally or directly into the systemic circulation. Its attractiveness resides in the fact that the mucosal membranes, upon which drug delivery systems are located, are readily accessible to patients or their caregivers. This means that the delivery technology can be precisely placed on the specific oral cavity membrane that is chosen as the site of absorption. It also means that the delivery system can be removed to terminate delivery if signs of adverse reactions are observed during treatment. The oral cavity represents a challenging area to develop an effective drug delivery technology. This arises due to the various inherent functions of the oral cavity (eating, swallowing, speaking, chewing), as well as the presence of the fluid that is involved in all these activities, saliva. This fluid is continually secreted into, and then removed from, the mouth. There are many advantages and disadvantages associated with the oral cavity as a site for drug delivery. Overall, however, it remains a viable option as a route for drug or nutraceutical administration and has been extensively studied for that purpose.

The oral mucosa route is a fast and effective way of delivering medication locally to the body and for the systemic administration of certain agents. Buccal administration refers to a topical route of administration by which drugs held or applied in the buccal area (in the cheek) diffuse through the oral mucosa (tissues which line the mouth) and enter directly into the bloodstream. Buccal administration may provide better bioavailability of some drugs and a more rapid onset of action compared to oral administration because the medication does not pass through the digestive system and thereby avoids first pass metabolism.

Sublingual (SL), from the Latin for "under the tongue", refers to the pharmacological route of administration by which substances diffuse into the blood through tissues under the tongue.

Many drugs are designed for sublingual administration such as cardiovascular drugs, steroids, barbiturates, opioid analgesics, enzymes, and increasingly vitamins and minerals.

Sublingual administration has certain advantages over oral administration. Being more direct, it is often faster, and it ensures that the substance will risk degradation only by salivary enzymes before entering the bloodstream, whereas orally administered drugs must survive passage through the hostile environment of the gastrointestinal tract, which risks degrading them, either by stomach acid or bile, or by the many enzymes therein, such as monoamine oxidase (MAO) or Trehalase. Furthermore, after absorption from the gastrointestinal tract, such drugs must pass to the liver, where they may be extensively altered; this is known as the first pass effect of drug metabolism. Due to the digestive activity of the stomach and intestines and the solubility of the GI tract, the oral route is unsuitable for certain therapeutic substances.

Ultimately, the decision to utilize the oral cavity as a site for drug delivery should be based on a comparison to other sites of delivery with regards to the following parameters: the clinical objectives of the treatment, the inherent physicochemical properties of the drug, the relative advantages of the route, product differentiation opportunities, the patient population, the cost of production and research and development time.

Two major routes of absorption are involved in oral mucosal drug permeation: the transcellular or intracellular route (where drugs permeate directly through the cells) and the paracellular or intercellular route (where drugs permeate by passive diffusion through the spaces between the cells). The paracellular route is favored especially by hydrophilic drugs such as peptides/proteins which dissolve more readily in the aqueous fluids filling the intercellular spaces.

Two factors influence the effectiveness of drug delivery from a delivery system designed for use in the oral cavity. The first is time of retention of the drug delivery system in contact with the oral mucosa; the second is the permeation rate of the drug across the oral mucosa.

The ability to retain the drug delivery system in contact with the oral mucosa at a location can be achieved through the incorporation of carefully selected muco-adhesive polymers into the formulation. This results in the delivery system having an intimate contact with the oral mucosa for a prolonged time. When muco-adhesive polymers rapidly and securely interact with the mucin molecules, found on the surface of the oral mucosa, it results in intimate contact of the dosage form with the mucosa. The prolonged contact time allows for a longer duration for absorption of the drug. It also reduces the pathway for diffusion of released drug between the surface of the delivery system and the surface of the mucosa. Muco adhesive polymers and penetration enhancers used for oral mucosal delivery have been extensively reviewed. Polymers such as alginate and chitosan are frequently used in such formulations.

Increasing the permeability of the drug through the oral mucosa is another approach used to assure therapeutic levels of a drug via the buccal route. This is commonly achieved using a penetration enhancer in the formulation. Various chemicals have been used as permeation enhancers. These include surfactants, bile salts, fatty acids and non-surfactants (such as cyclodextrins, and chitosan).

The examples which follow are intended in no way to limit the scope of the disclosure but are provided to illustrate how to prepare and use compounds disclosed herein. Many other embodiments of this disclosure will be apparent to one skilled in the art. Examples of how the Trehalose can be delivered via oral mucosa are summarized below:

Sublingual tablets—tablets which easily melt in the mouth, dissolve rapidly and with little or no residue. Nitroglycerine tablets are an example, the anti-emetic;

Sublingual strips—like tablets in that they easily melt in the mouth and dissolve rapidly. Suboxone® is an example of medication that comes in a sublingual strip;

Multi-Purpose Tablets—Soluble tablets for either oral or sublingual administration, often also suitable for preparation of injections, Hydrostat® and several brands of morphine tablets and cubes;

Sublingual Drops—a concentrated solution to be dropped under the tongue, as with some nicocodeine cough preparations;

Sublingual Spray—spray for the tongue; certain human and veterinary drugs are dispensed as such;

Lozenge—effects a metered and patient-controlled-rate combination of sublingual, buccal, oral mucosa administration, as with the Actiq® fentanyl lozenge-on-a-stick (lollipop);

Effervescent Buccal or Sublingual Tablets—this method drives the drug through the mucous membranes much faster (this is the case in the stomach with carbonated or effervescent liquids as well) and is used in the Fentora® fentanyl buccal tablet.

Almost any form of substance may be amenable to sublingual administration if it dissolves easily in saliva. Powders and aerosols may all take advantage of this method. Several factors, such as pH, molecular weight, and lipid solubility, however, may determine whether the route is practical. Based on these properties, a suitably soluble drug may diffuse through the mucosa to be effective especially Trehalose that is water soluble.

Some of the advantages of using oral delivery versus IV or oral ingestion administration are: less drug could be required compared to IV or ingestion administration, onset of action can be more rapid via oral mucosa compared to the oral route adverse effects are potentially less severe and less frequent drugs that are not absorbed or enzymatically degraded can be delivered via oral mucosa compared to injectable dosage forms, and oral drug therapy is painless and relatively comfortable for the patient which encourages compliance.

Those that are more hydrophilic are absorbed within minutes to tens of minutes. In the present invention, a delivery system, as mentioned above, is filled with a therapeutic dose of Trehalose, which is highly water soluble and hydrophilic, for delivery to oral mucosa of a therapeutic dose to stimulate autophagy for the treatment of chronic cardiovascular or neurodegenerative degenerative diseases. The dose can range from 1 to 5000 milligrams with 25 to 200 milligrams being preferred. Trehalose, like most sugars, can be absorbed from the oral mucosa into the bloodstream within minutes or hours after contact with the oral mucosa. Oral mucosa administration of Trehalose, therefore, can be multiple times a day or more infrequently depending on its autophagy efficacy on a per patient basis. Capsules, tablets, films and the like of the present invention are manufactured by numerous companies that can produce the product cost effectively and in large volumes.

Alternatively, the inhalation route is a fast and effective way of delivering medication locally to the lungs and for the systemic administration of certain agents. Inhalation drug therapy is used extensively to treat respiratory conditions such as asthma and Chronic Obstructive Pulmonary Disease (COPD). Recently, it has been shown that pulmonary drug delivery could also be an effective route to deliver drugs to the systemic circulation thanks to the large surface area of the lungs with highly vascularized epithelia. Research is ongoing to develop inhalation systems to treat neurological disorders, cystic fibrosis, pain management and to deliver vaccines.

The examples which follow are intended in no way to limit the scope of the disclosure but are provided to illustrate how to prepare and use compounds disclosed herein. Many other embodiments of this disclosure will be apparent to one skilled in the art.

A dry-powder inhaler (DPI) is a device that delivers medication to the lungs in the form of a dry powder. DPIs are commonly used to treat respiratory diseases and other conditions such as asthma, bronchitis, emphysema and COPD although DPIs (such as inhalable insulin Afrezza®, MannKind Corporation, Westlake Village, Calif., USA) have also been used in the treatment of diabetes mellitus.

DPIs are an alternative to the aerosol-based inhalers commonly called metered-dose inhaler (or MDI). The DPIs may require some procedure to allow a measured dose of powder to be ready for the patient to take. The medication is commonly held either in a capsule for manual loading or a proprietary form inside the inhaler. Once loaded or actuated, the operator puts the mouthpiece of the inhaler into their mouth and takes a sharp, deep inhalation (ensuring that the medication reaches the lower parts of the lungs), holding their breath for 5-10 seconds. There are a variety of such devices. The dose that can be delivered is typically less than a few tens of milligrams in a single breath since larger powder doses may lead to provocation of cough. Most DPIs rely on the force of patient inhalation to entrain powder from the device and subsequently break-up the powder into particles that are small enough to reach the lungs. For this reason, insufficient patient inhalation flow rates may lead to reduced dose delivery and incomplete deaggregation of the powder, leading to unsatisfactory device performance. Thus, most DPIs have a minimum inspiratory effort that is needed for proper use and it is for this reason that such DPIs are normally used only in older children and adults.

Figure 1:
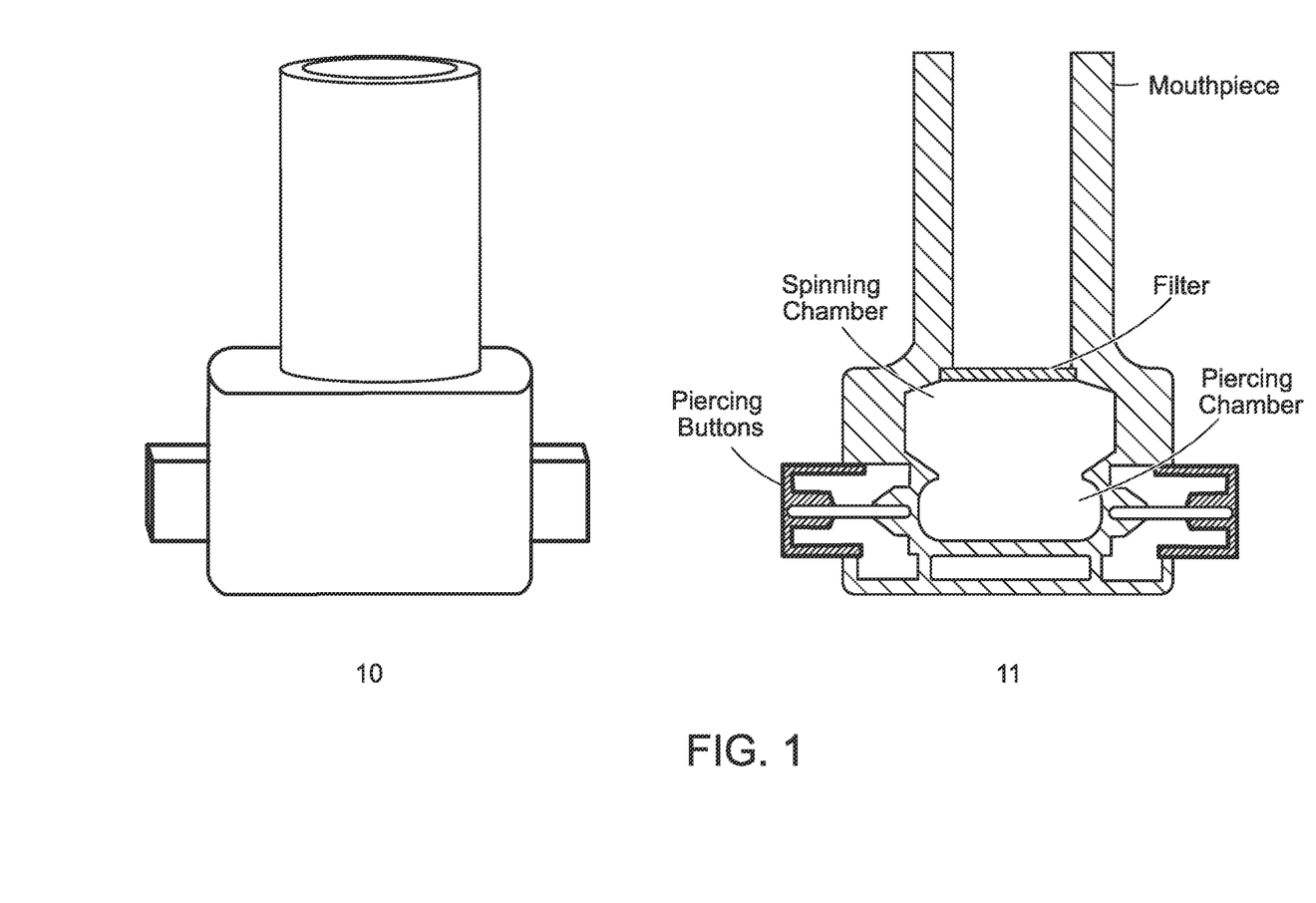
Figure 2:
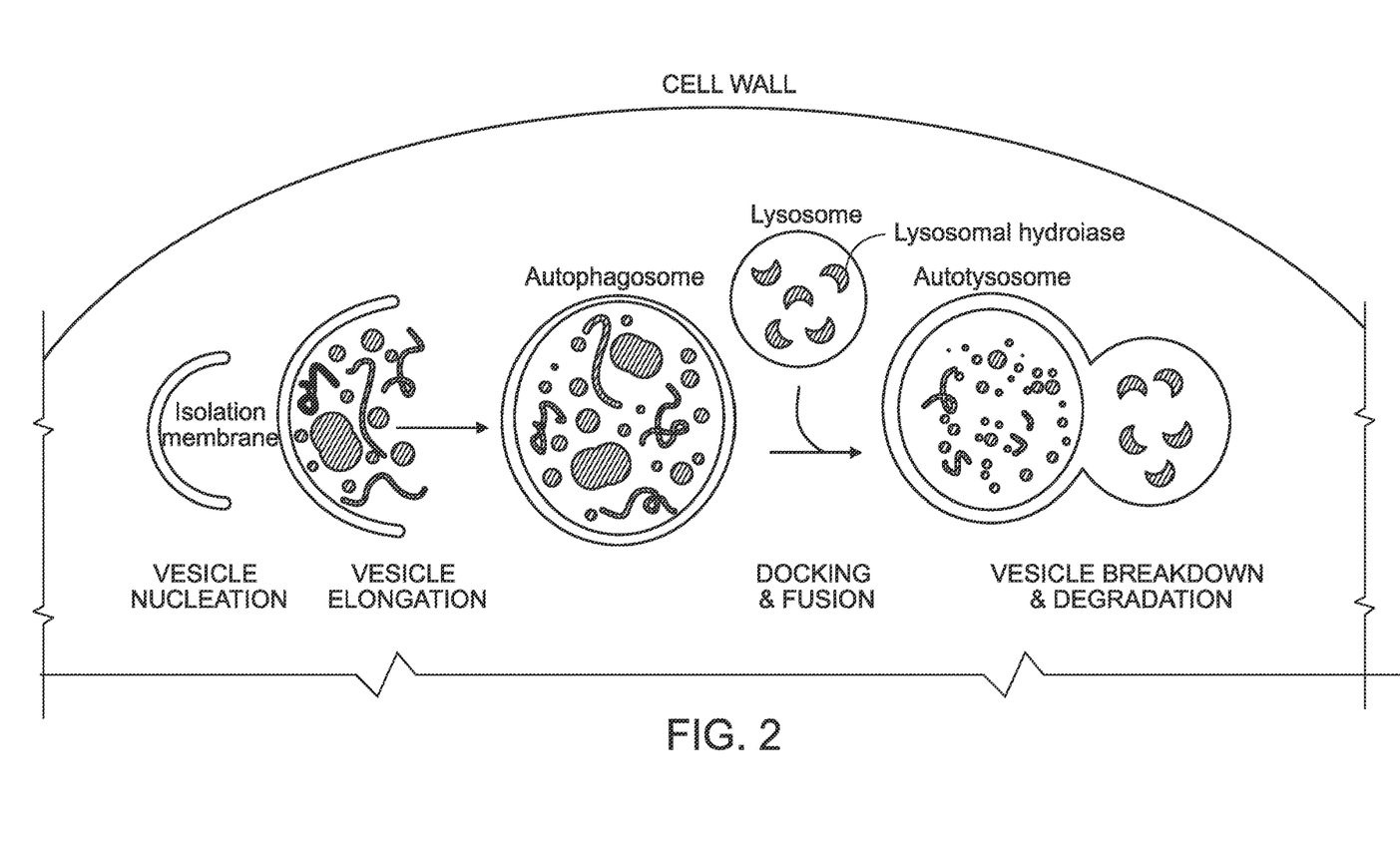
Figure 3:
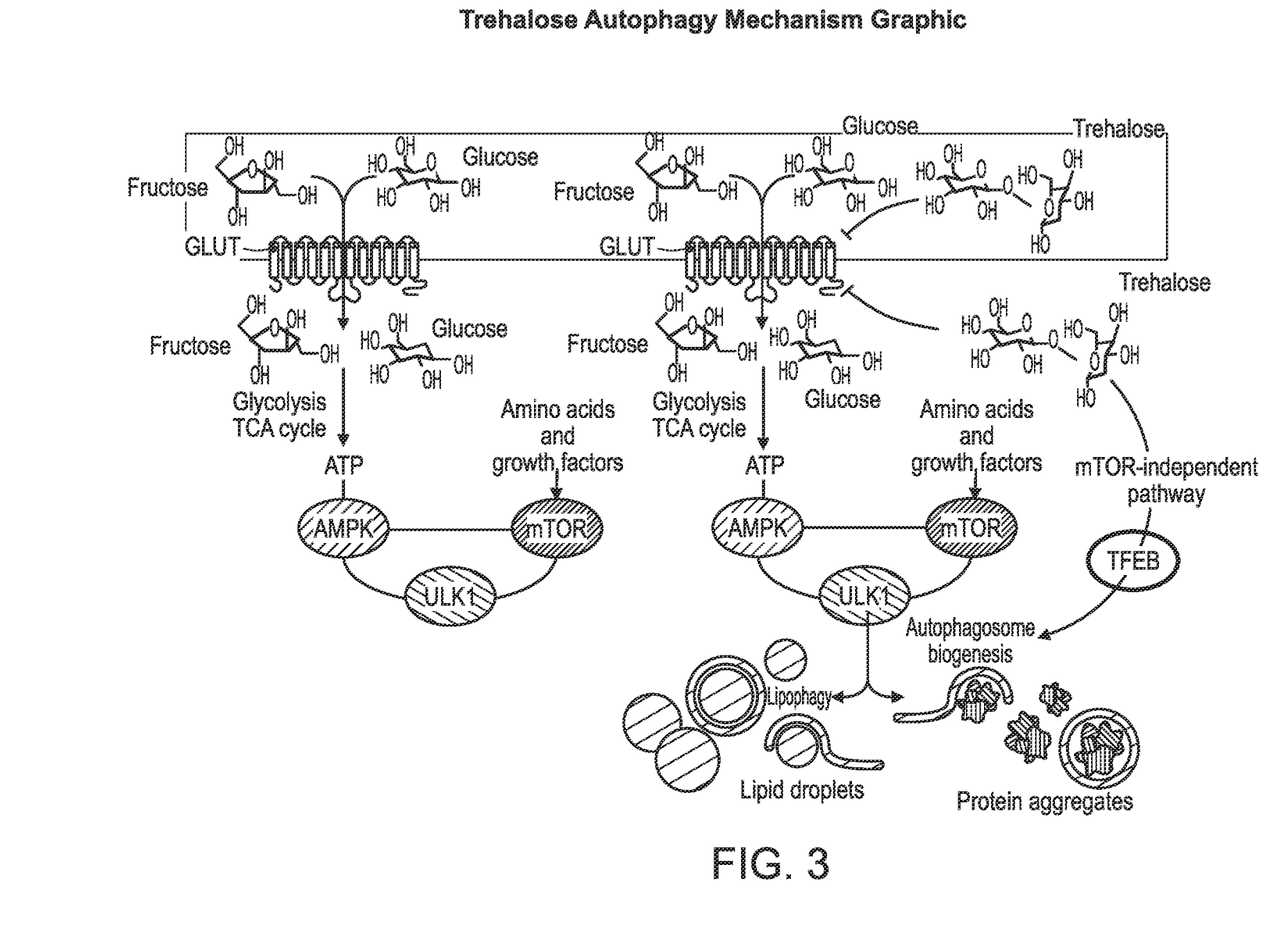

FIG. 1 shows an exterior side view 10 and a cross sectional view 11 of a simple DPI utilized in the present invention to administer autophagy stimulating Trehalose. The use of DPIs is well known and DPIs are commercially available from numerous sources. In an example of the present invention, a DPI is utilized for delivery of Trehalose to the lungs for subsequent absorption into the blood stream. A capsule containing the therapeutic of interest is loaded into the piercing chamber and is subsequently pierced and the released micro powder is inhaled by the patient into the lung via a deep breath.

Some of the advantages of using a DPI versus oral administration are: less drug could be required compared to oral administration, onset of action can be more rapid via inhalation compared to the oral route adverse effects are potentially less severe and less frequent drugs that are not absorbed orally can be delivered via the lung and compared to injectable dosage forms, inhaled drug therapy is painless and relatively comfortable for the patient which encourages compliance.

No non-invasive route of delivery provides the speed of action that an inhaled drug can provide. One of the advantages of inhaled drugs is that it that they more rapidly absorbed than subcutaneously injected molecules and provides a more immediate physiological response. Small molecules, particularly hydrophobic molecules, are absorbed within seconds after inhalation and can thus be used to treat a wide variety of symptoms that come on suddenly or need long term administration. Pain, panic, anxiety, nausea, cardiovascular crises, bronchoconstriction, sleep induction, spasms, Parkinson's lock-up, and hot flashes are some of the rapid-onset conditions that are addressable with inhaled medicines.

Most small molecules that have some water solubility are rapidly and efficiently absorbed from the lungs. Those that are more hydrophobic are absorbed even more rapidly within seconds to a few minutes. Those that are more hydrophilic are absorbed within minutes to tens of minutes. In one example of the present invention, a capsule is filled with a therapeutic dose of Trehalose, which is highly water soluble and hydrophilic, for delivery to the lungs of a therapeutic dose to stimulate autophagy for the treatment of chronic cardiovascular or neurodegenerative degenerative diseases. The dose can range from 1 to 1000 milligrams with 25 to 200 milligrams being preferred. Trehalose, like most sugars, can be absorbed from the lungs into the bloodstream within 2 hours of inhalation. DPI administration of Trehalose, therefore, can be multiple times a day or more infrequently depending on its autophagy efficacy on a per patient basis. Capsules of one example of the present invention are manufactured by Capsugel (Morristown, N.J., USA).

Synthesis

The Trehalose used in an example of the present invention is formed generally by spray drying resulting in sub 100-micron diameter particles and preferably less than 10 microns. The particles are then formulated with appropriate adjuvants into a final formulation for dry particle delivery. By combining well-defined raw materials, particle engineering, and precise process controls, it is possible to produce inhalation-grade Trehalose particles with uniform sizes of approximately 2.5 μm and average diameters of less than 2 The active ingredients (AI) of the particles can exceed 90% of the total powder mass and the AI can exceed 80% using DPIs.

The homogeneity of the powder (i.e., dose uniformity) is ensured by the physical integration of carrier excipients with the AI an attribute inherent to the spray dry formulation process. The powders are then filled into a capsule made from either gelatin or some cellulose co-polymer for loading into the DPI device for administration. Additionally, from time to time, it may be desirable to add additional therapeutic molecules to the formulation to act synergistically or amplify the autophagy generated by the Trehalose. Anti-inflammatory additives such as steroids or rapamycin would be acceptable candidates to add into a formulation.

Provided here is a composition comprising a disclosed compound and pharmaceutically acceptable excipient or carrier suitable for sublingual/buccal administration, intranasal administration or a composition suitable for inhalation (including vaping).

Dosages

Trehalose as a food additive is safe to use. It is Generally Recognized As Safe (GRAS) by the U.S. Food and Drug Administration. Trehalose is approved and commonly used in Japan, Taiwan and South Korea and is approved in the European Union, Australia and New Zealand.

The dosage of any disclosed compositions will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions may be readily determined by techniques known to those of skill in the art or as taught herein.

In certain embodiments, the dosage of the subject compounds will generally be in the range of about 1 to 1000 milligrams depending on the body weight of the patient, specifically in the range of about 25 to 200 milligrams.

An effective dose or amount, and any possible effects on the timing of administration of the formulation, may need to be identified for any particular composition of the disclosure. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically re-evaluated to determine the extent of improvement by measuring the same parameters. Adjustments to the amount(s) of subject composition administered and possibly to the time of administration may be made based on these re-evaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions because the onset and duration of effect of the different agents may be complimentary.

Therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the disclosure, the therapeutically effective dose may be estimated initially from cell culture assays.

Formulations

Pharmaceutical compositions of the disclosure may be administered by various means, depending on their intended use, as is well known in the art. For example, if compositions of the disclosure are to be administered sublingually/buccally, they may be formulated as tablets, capsules, granules, powders or syrups. Alternatively, formulations disclosed herein may be administered drop infusion preparations or suppositories. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent. The disclosed excipients may serve more than one function. For example, fillers or binders may also be disintegrants, glidants, anti-adherents, lubricants, sweeteners and the like.

In formulations of the disclosure, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

The formulations may conveniently be presented in unit dosage form and may be prepared by any methods well known in the art of pharmacy. The amount of a composition that may be combined with a carrier material to produce a single dose vary depending upon the subject being treated, and the particular mode of administration.

Methods of preparing these formulations include the step of bringing into association compositions of the disclosure with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for sublingual/buccal administration may be in the form of capsules, cachets, pills, tablets, films, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the disclosure may also be administered as a bolus, electuary, or paste.

In solid dosage forms for sublingual/buccal administration (capsules, tablets, pills, dragees, powders, granules and the like), the subject composition is mixed with one or more pharmaceutically acceptable carriers, such as sodium citrate or di-calcium phosphate, and/or any of the following: (1) fillers or extenders, such as starches, dextrose, lactose, sucrose, glucose, mannitol, and/or silicic acid; (2) binders, such as, for example, celluloses (e.g., microcrystalline cellulose, methyl cellulose, hydroxypropylmethyl cellulose (HPMC) and carboxymethylcellulose), alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like. The disclosed excipients may serve more than one function. For example, fillers or binders may also be disintegrants, glidants, anti-adherents, lubricants, sweeteners and the like.

Formulations and compositions may include micronized crystals of the disclosed compounds. Micronization may be performed on crystals of the compounds alone, or on a mixture of crystals and a part or whole of pharmaceutical excipients or carriers.

A tablet may be made by compression or molding, optionally with one or more accessory ingredients. Compressed tablets may be prepared using binder (for example, gelatin, microcrystalline cellulose, or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. The disclosed excipients may serve more than one function. For example, fillers or binders may also be disintegrants, glidants, anti-adherents, lubricants, sweeteners and the like.

It will be appreciated that a disclosed composition may include lyophilized or freeze-dried compounds disclosed herein. For example, disclosed herein are compositions that disclosed compounds crystalline and/or amorphous powder forms. Such forms may be reconstituted for use as e.g., an aqueous composition.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It should be noted that excipients given as examples may have more than one function. For example, fillers or binders can also be disintegrants, glidants, anti-adherents, lubricants, sweeteners and the like.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

It will be appreciated that contemplated formulations, such as oral formulations (e.g. a pill or tablet), may be formulated as controlled release formulation, e.g., an immediate release formulation, a delayed release formulation, or a combination thereof.

Trehalose may be combined with other known therapeutics to amplify autophagy systemic effects of an individual by combining with an immune suppressive drug such as rapamycin (marketed under the trade name Rapamune® (Pfizer, Inc., New York, N.Y., USA)) and/or metformin (marketed under the trade name Glucophage® (Merck KGaA, Lyon, FR)).

Kits

This disclosure also provides kits for conveniently and effectively implementing the methods disclosed herein. Such kits comprise any subject composition, and a means for facilitating compliance with methods disclosed herein. Such kits provide a convenient and effective means for assuring that the subject to be treated takes the appropriate active in the correct dosage in the correct manner. The compliance means of such kits includes any means which facilitates administering the actives according to a method disclosed herein. Such compliance means include instructions, packaging, and dispensing means, and combinations thereof. Kit components may be packaged for either manual or partially or wholly automated practice of the foregoing methods. In other embodiments involving kits, the disclosure contemplates a kit including compositions disclosed herein, and optionally instructions for their use.

Equivalents

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

The above discussion is meant to be illustrative of the principle and various embodiments of the present invention. Numerous variations and modifications will become apparent to those skilled in the art once the above disclosure is fully appreciated. It is intended that the following claims be interpreted to embrace all such variations and modifications.

What is claimed:

1. A pharmaceutically acceptable composition consisting of trehalose or one or more of pharmaceutically acceptable salt thereof and a pharmaceutically acceptable excipient and pharmaceutically acceptable carrier;
   wherein the pharmaceutically acceptable composition is a dry powder delivered directly to the lungs of a patient; and
   wherein said composition contains trehalose or a pharmaceutically-acceptable salt thereof in an amount sufficient to stimulate autophagy in said patient;
   wherein said trehalose or a pharmaceutically acceptable salt thereof comprises particles with uniform sizes of approximately 2.5 μm or average diameters of less than 2 μm;
   wherein the pharmaceutically acceptable composition comprises 90% trehalose;
   wherein said pharmaceutically acceptable composition is formulated so that said patient receives a dose of trehalose ranging from 25 to 200 milligrams;
   wherein said trehalose is not adhered to the surface of a carrier particle.

2. The pharmaceutically acceptable composition according to claim 1, wherein said composition is delivered to a patient in need thereof as an aerosol into the lungs of the patient.

3. The pharmaceutically acceptable composition according to claim 1, wherein said patient suffers from a cardiovascular, liver or neurodegenerative disease.

4. The pharmaceutically acceptable composition according to claim 3, wherein said patient suffers from a disease selected from the group consisting of cardiovascular atherosclerosis, Parkinson's disease, Huntington's disease, Amyotrophic lateral sclerosis and Alzheimer's disease.

5. The pharmaceutically acceptable composition according to claim 1, wherein said dose is between 25 to 150 milligrams.

6. The pharmaceutically acceptable composition according to claim 1, wherein the particle size of said pharmaceutically acceptable composition is less than 10 microns.

7. The pharmaceutically acceptable composition according to claim 1, wherein said pharmaceutically acceptable composition is delivered to the patient using a dry-powder inhaler.

8. The pharmaceutically acceptable composition according to claim 1, wherein said pharmaceutically acceptable composition is delivered to the patient using a measured-dose inhaler.

* * * * *